United States Patent [19]

Bernath

[11] Patent Number: 4,684,509
[45] Date of Patent: Aug. 4, 1987

[54] APPARATUS FOR MEASURING GAS CONCENTRATIONS IN A HOT GAS SAMPLE WITHDRAWN FROM A PROCESS CHAMBER

[76] Inventor: Tibor Bernath, Distelborn 6, 3000 Hannover 91, Fed. Rep. of Germany

[21] Appl. No.: 755,515

[22] Filed: Jul. 16, 1985

[30] Foreign Application Priority Data

Jul. 17, 1984 [DE] Fed. Rep. of Germany ....... 3426329

[51] Int. Cl.⁴ ............................................ G01N 30/68
[52] U.S. Cl. ..................................... 422/54; 324/468; 422/70; 422/80; 436/154
[58] Field of Search ......................... 422/54, 70, 78, 80; 73/863.11, 23.1; 436/154; 324/468, 469

[56] References Cited

U.S. PATENT DOCUMENTS

| 3,095,278 | 6/1963 | Green, Jr. | 422/54 |
| 3,658,481 | 4/1972 | Guillemin et al. | 422/54 |
| 3,661,533 | 5/1972 | David et al. | 436/154 |
| 3,917,454 | 11/1975 | Clark | 73/863.11 |
| 4,069,018 | 1/1978 | Karna et al. | 436/154 |
| 4,211,746 | 7/1980 | Mees | 422/54 |
| 4,262,533 | 4/1981 | Jaeger | 73/863.11 |
| 4,311,664 | 1/1982 | Zaremba et al. | 422/54 |
| 4,344,917 | 8/1982 | Schorno | 73/863.11 |
| 4,466,943 | 8/1984 | Murase et al. | 422/54 |
| 4,471,664 | 9/1984 | Mailuet et al. | 73/863.11 |

FOREIGN PATENT DOCUMENTS 7012403  2/1972  Netherlands .................... 73/863.11

Primary Examiner—Michael S. Marcus
Attorney, Agent, or Firm—Pennie & Edmonds

[57] ABSTRACT

An apparatus for measuring a gas concentration in a hot gas sample withdrawn from a process chamber, comprising a metal block (10) adapted to be tempered and housing at least the detector (12) and those components of the flow path guiding the gas to be measured between a sampling probe and the detector. A suction pump (14) sucks the gas sample into the metal block (10) where the gas to be measured is divided into two conduits. The first conduit leads to the detector and the second conduit back to the process chamber.

16 Claims, 3 Drawing Figures

APPARATUS FOR MEASURING GAS CONCENTRATIONS IN A HOT GAS SAMPLE WITHDRAWN FROM A PROCESS CHAMBER

The invention relates to an apparatus for measuring especially the hydrocarbon concentration in a hot gas sample withdrawn drawn from a process chamber and for generating an electric monitoring signal in accordance with the concentration, comprising a sampling probe which is tempered and adapted to be introduced into the process chamber, a hydrocarbon detector arranged outside of the process chamber adjacent the wall thereof, for instance a flame ionization detector, a suction pump for the withdrawal of the gas sample, and a thermally insulating casing enclosing the parts mentioned outside the process chamber. Such apparatus, as described in my earlier U.S. Pat. No. 4,342,234, are used, for example, in monitoring the hydrocarbon concentration in drying oven compartments of industrial paint shops. In such process chambers the hydrocarbon concentration must not exceed certain values if the risk of explosion is to be avoided. If the measuring device determines that the concentration has risen above the admissible value, the plant is shut down.

The gas sample withdrawn from the process chamber often has a temperature of 250° C. and higher so that it must be made sure that the gas does not contact colder surfaces on its way to the detector where the organic vapors might condense. For this reason it is preferred to place the hydrocarbon detector next to the wall of the process chamber, thus providing the shortest possible path of conveyance of the gas sample from the chamber to the detector. All those component parts which come into contact with the gas sample must be tempered uniformly and without any delay in order to avoid the condensation of organic substances as that would introduce considerable error into the measuring results. This is difficult to achieve. Since air is a poor heat conductor no homogeneous temperature distribution of the individual components is warranted specifically if the gas sample having passed the sample probe is introduced into an analyzing compartment in which the gas conducting members are tempered by hot air.

It is another disadvantage of known apparatus of the kind in question that a condensate is formed at the detector as the gas sample leaves the same after having been analyzed.

It is an object of the invention to develop the apparatus of the kind specified initially such that the hydrocarbon concentration of the gas sample measured by means of the detector corresponds exactly to that in the process chamber.

This object is met, in accordance with the invention, in that a solid metal block adapted to be tempered is provided in the casing and houses at least the detector and the components guiding the gas to be measured in the flow path between the sampling probe and the detector, the flow paths being embodied by bores in the metal block.

In a preferred embodiment of the invention the metal block also comprises the suction pump which thus may be disposed in the path of conveyance of the gas between the chamber and the detector.

As the metal block adapted to be tempered in accordance with the invention has a homogeneous temperature distribution because of the good thermal conductivity of the metal and contains all those parts conducting gas to be measured in the flow path between the sampling probe and the detector, it is assured that all component parts which will be contacted by the gas to be measured have the temperature of the metal block, whereby no condensations can occur which would falsify the result of the measurement.

The metal block may be formed integrally in one piece, and the individual components, like the detector, the suction pump, a gas filter, etc. are adapted to be inserted into bores formed in the metal block.

In the case of a preferred embodiment of the invention the metal block consists of two separable members, one of which houses the detector and the other one the suction pump. The two members are adapted to be connected with good thermal contact so that a single heater is sufficient for uniform heating of the entire metal block.

The heating capacity required to heat up the metal block may be reduced by enclosing the same all around by an insulation.

Typically, the detector used with an apparatus according to the invention is a conventional flame ionization detector with which an electric field is applied to a pure hydrogen flame to which air free of hydrocarbon is supplied while it burns. The gas sample is introduced into the flame and this causes considerable ion formation resulting in a flux of current in the electric field applied. The reinforced current signal is an indication of the concentration of hydrocarbons in the gas sample.

The amount of gas to be introduced into the flame is rather small, normally amounting to some 20 ml/min.

To obtain an accurate measuring result, a preferred modification of the invention provides for a much greater quantity of gas to be withdrawn from the process chamber by the suction pump. At the pressure end of the suction pump the gas is divided into two conduits, a first one leading to the detector and a second one returning to the process chamber. The gas flow in the second conduit is much greater than in the first one which passes the gas to the flame.

The conduits each are provided with capillary tubes in order to establish stable flow conditions.

In a preferred further development of the invention the safety of the measuring apparatus is increased by a pressure switch provided at the pressure end of the suction pump to furnish a disturbance signal if the pump pressure head drops.

A modified embodiment of the invention comprises a control air system in order to stabilize the pressure at the pressure end of the suction pump and to maintain the gas flow constant in the first conduit leading to the detector flame. By means of a pressure reducer this system makes sure that the flow is constant in the second conduit.

In accordance with a preferred further development of the invention it is provided for reliable and repeatable gauging of the detector that a connection for an hydrocarbon-free gas as well as a connection for a gas of a defined hydrocarbon concentration may be caused to communicate with the flame, apart from the connections for the combustion gas ($H_2$) of the flame and the combustion air. The gas which is free of hydrocarbon may be clean air.

Complete and fully automatic self-control of the measuring apparatus is achieved by a further development of the invention is achieved by a further development of the invention in that a signal is released if the quantity of the gas sample withdrawn fails to reach a predetermined value. Thus it is guaranteed that gas from the process chamber is permanently being analyzed in the flame of the detector.

The safety of the apparatus also may be improved by monitoring the detector output signal for a desired value so as to give an alarm signal if, for instance, the detector or the suction pump should fail.

The invention will be described further, by way of example, with reference to the accompanying drawings, in which.

Figure 1:
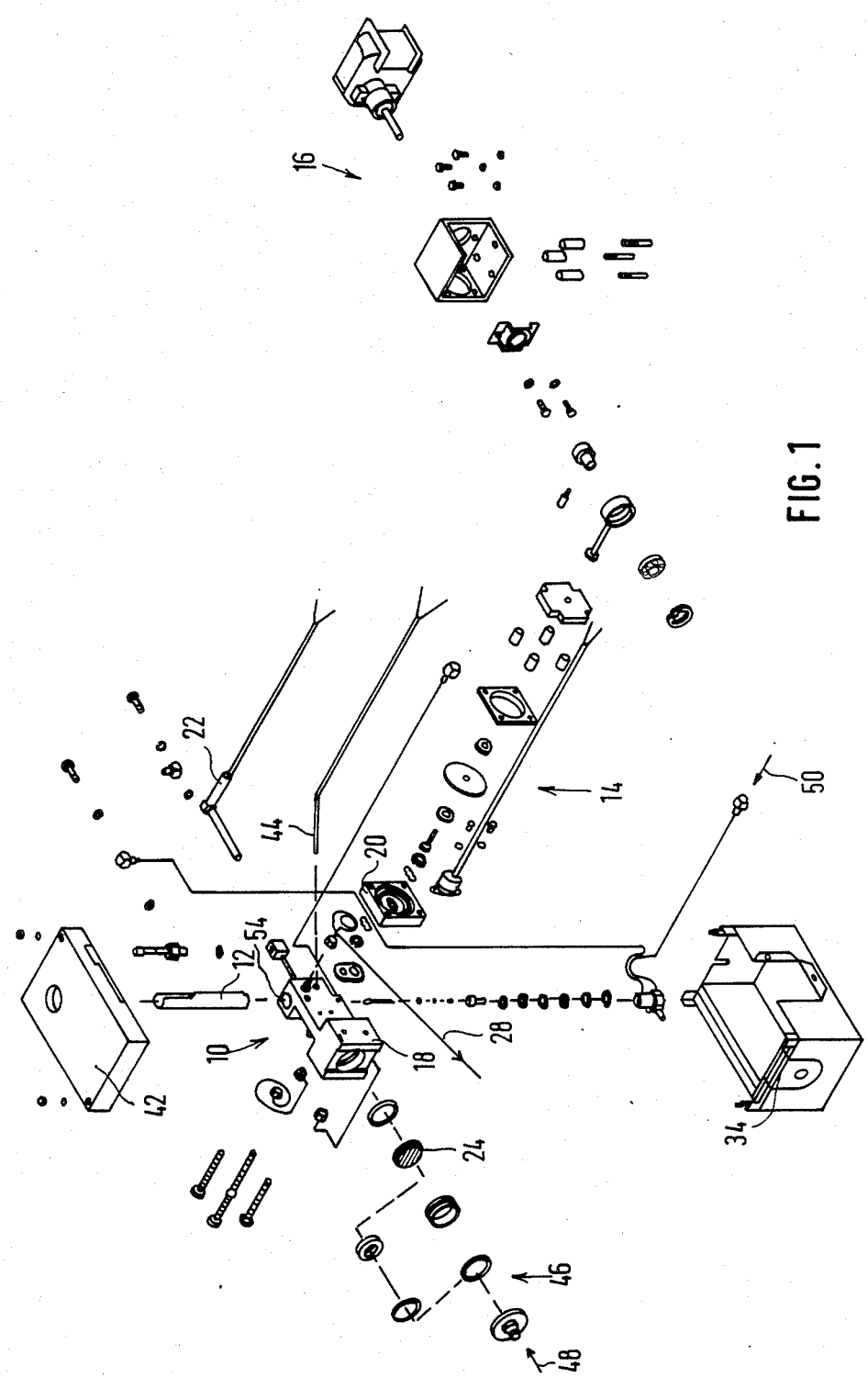
FIG. 1 is an exploded view of a measuring apparatus according to the invention.

FIG. 1 shows the metal block 10 of the measuring apparatus into which the detector 12 (a flame ionization detector) is introduced by sliding. The metal block 10 is mounted directly adjacent the wall of the process chamber (not shown) and comprises a suction pump 14 to withdraw the gas sample by way of a sampling probe (not shown) out of the process chamber and into the metal block 10. The drive of the suction pump 14 is marked by reference numeral 16 in FIG. 1.

Figure 2:
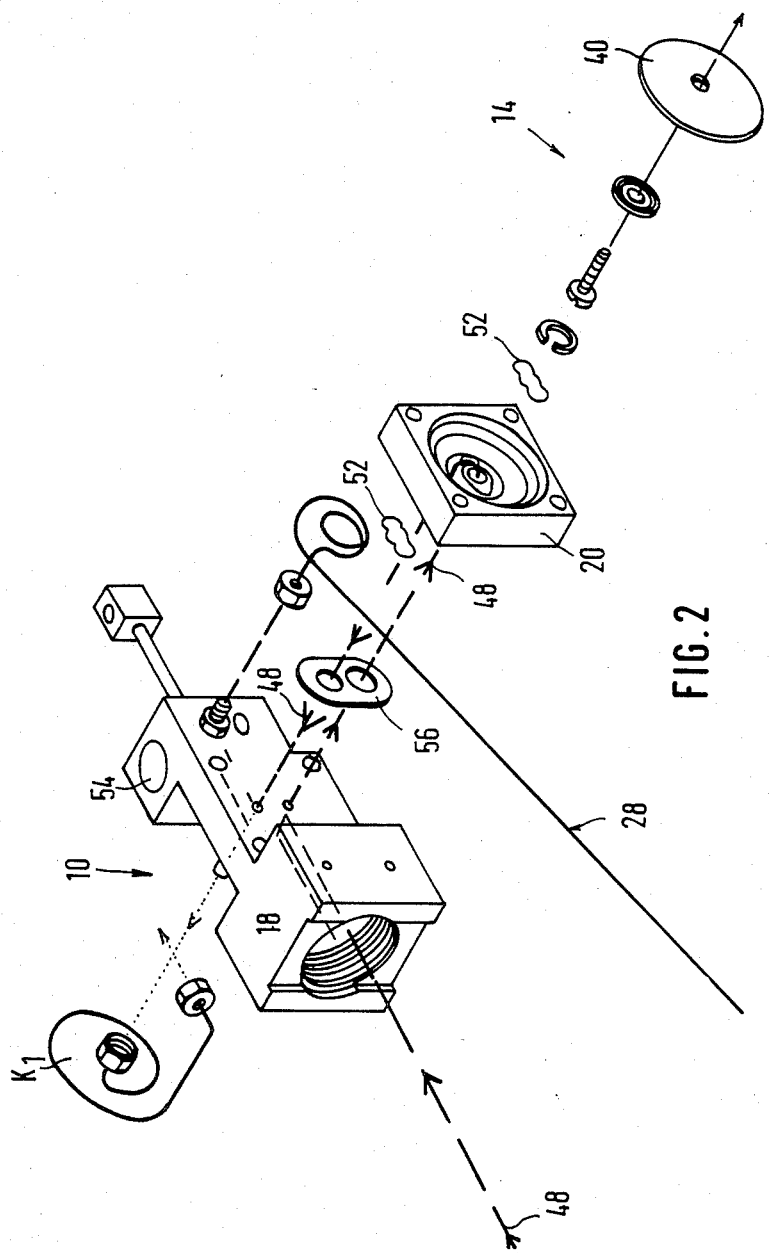
FIG. 2 is an exploded view in greater detail of the metal block of the measuring apparatus.

As shown in FIGS. 1 and 2, the metal block 10 is divided into two members 18 and 20 which are adapted to be connected in good thermal contact by screws. A heater 22 may be slid into the metal block member 18 for homogeneous heating of the entire metal block.

A gas filter 24 is secured by seals and clamping rings 46 in the metal block 10 and is positioned in the initial part of the flow path of the gas to be measured, indicated by arrow 48. In accordance with FIG. 1 the gas thus enters the metal block 10 in the direction of arrow 48.

FIG. 2 shows the further course of the flow path of the gas to be measured as it passes on through the apparatus, again as marked by arrow 48. The gas to be measured is conveyed by the suction pump 14 housed in the metal block member 20 and being designed as a diaphragm pump which includes a diaphragm 40, the gas passing through the metal block and the capillary tube K1 to reach the flame detector 12 which is slid into the bore 54 in the metal block 10. FIG. 1 shows an insulation 34 including a top cover 42 all around the metal block 10. In this manner the heating performance can be reduced which is required of the heater 22. A temperature sensor 44 determines the temperature of the metal block 10. The two members 18,20 of the metal block 10 are adapted for connection by a seal 56 in such manner that member 20 of the metal block assumes the temperature of metal block member 18 without delay.

Figure 3:
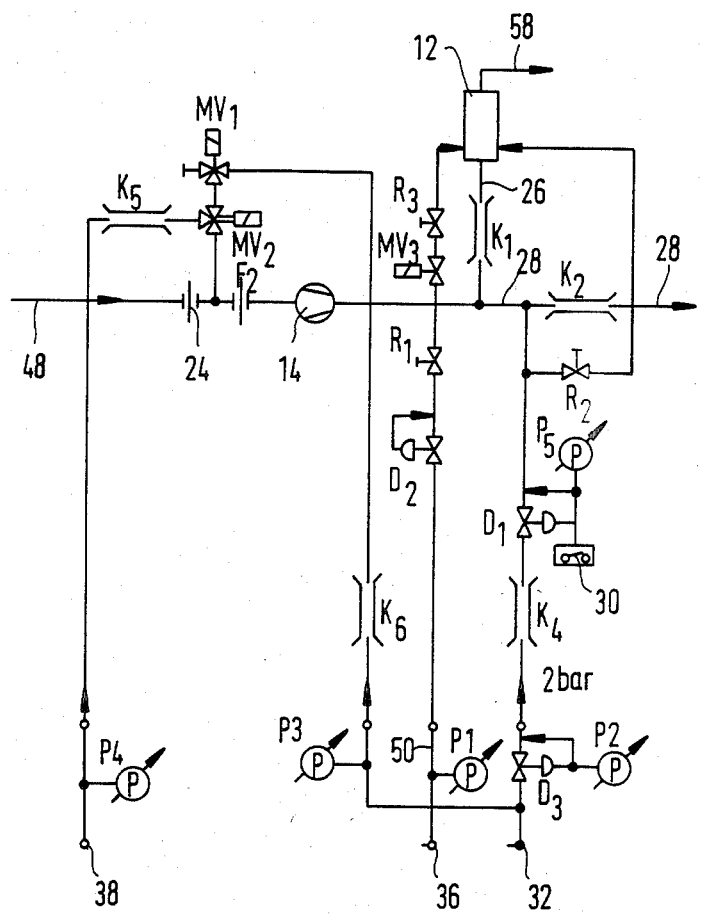
FIG. 3 is a diagram of the gas conduit system of the measuring apparatus.

FIG. 3 is diagrammatic presentation of the flow conditions of the gas to be measured and of the other gases. The gas to be measured enters the metal block 10 in accordance with arrow 48 (see also FIGS. 1 and 2) under the action of the suction pump 14 and passing through the filter 24. At the pressure end of the suction pump 14 the gas stream is divided into two portions. A smaller gas flow of approximately 20 ml/min. enters the conduit 26 comprising the capillary tube K1 and flows to the detector 12 where it is subjected to the flame of the flame ionization detector. The greater portion of the gas stream aspired of about 1.6 l/min. flows through the conduit 28 including capillary tube K2 and returns to the process chamber (not shown).

The amount of gas which reaches the detector 12 depends on the pressure differential at the capillary tube K1. The secondary end of the capillary tube K1 communicates with the detector 12 and is practically exposed to atmospheric pressure. Consequently the amount of gas which flows through the capillary tube K1 mainly is a function of the pressure prevailing at the primary end and determined by the pressure head of the suction pump 14. This pressure head of the suction pump, however, may vary in response to some measuring magnitudes, such as the filter resistance to the gas to be measured, the delivery of the suction pump, etc. Therefore, an air control system is built in to stabilize the quantity of gas to be measured which flows through the capillary tube K1. The system substantially consists of capillary tube K4 and pressure reducer D1. The capillary tube K2 is so dimensioned that a pressure head of about 0.2 bar is produced if the pump delivery is approximately 1.6 l/min. and the air control quantity is adjusted by the pressure reducer D1 to some 0.8 l/min. If the delivery of suction pump 14 drops to a minimum of approximately 0.8 l/min., the pressure reducer D1 automatically resumes control, adjusting the pressure head to 0.2 bar. If the quantity delivered by the suction pump continues to drop, the pressure reducer D1 still attempts to achieve control. Yet this requires ever rising rates of flow through the capillary tube K4. At a certain pressure drop downstream of the suction pump, the amount of gas flowing through the capillary tube K4 will no longer be sufficient so that a minimum input pressure is no longer reached at the pressure reducer D1. As a consequence there will be a distinct drop in pressure head downstream of the suction pump. This pressure reduction is sensed by the pressure switch 30 and indicated as a disturbance.

In FIG. 3 reference numerals K1 to K5 designate capillary tubes in general which are associated with respective conduits. Reference numerals P1 to P5 designate pressure gauges serving to measure the gas pressure at different locations in the system of conduits. Reference numerals R1 to R3 designate individual valves, while magnetic valves are designated MV1 to MV3.

Gauging of the measuring apparatus, in other words the coordination of the flow measured by the flame ionization detector with a certain hydrocarbon concentration in the gas subjected to the sampling will be described below with reference to FIG. 3. The apparatus comprises three gas connections 32, 36, and 38 (apart from the connection for the gas sample as per arrow 48). Connection 32 may be used for metered supply of pressurized air to the apparatus, which air one the one hand serves as combustion air for the continuous operation of the flame and, on the other hand, for being free of hydrocarbon, is suitable also for gauging the detector 12. The combustible gas (H$_2$) of the flame is introduced into the apparatus through the connection 36, while connection 38 may be used for feeding the flame of the detector with a so-called gauging gas, i.e. a gas having a defined hydrocarbon concentration. The gauging of the detector is effected by successively admitting two comparative gases, namely the gas which is free of hydrocarbon and the gauging gas. Admission of the gases is permitted by actuating the magnetic valves MV1 and MV2. The metering of the gauging gases is such that more gas is introduced into the apparatus than the suction pump can convey. The surplus gas flows backwards, against the direction of the arrow 48, into the process chamber.

Valve R2 serves for adjustment of the amount of combustion air. The pressure reducer D1 and the valves R1 and R3 serve for adjustment and maintenance of the combustible gas flow toward the flame. The combustible gas flows through the connection 36 and the conduit 50.

What is claimed is:

1. In an apparatus for measuring hydrocarbon concentration in a hot gas sample withdrawn from a process chamber wherein said hot gas is present and for generating an electric monitoring signal in accordance with said concentration, comprising a tempered sampling probe for introduction into a process chamber, a hydrocarbon detector arranged outside of and adjacent a wall of a process chamber, a suction pump having a suction end and a pressure end for withdrawing said gas sample, a thermally insulating casing enclosing said detector and said suction pump, the improvement comprising a tempered solid metal block enclosed in said casing, said solid metal block housing therein at least said detector and said suction pump and having supply conduits for directing the gas to be measured to said detector from the process chamber, said supply conduits being defined by bores in the metal block.

2. In the apparatus as claimed in claim 1, the improvement wherein the metal block is formed integrally in one piece.

3. In the apparatus as claimed in claim 1, the improvement wherein the metal block comprises at least two separable members, one of which houses the detector and the other one the suction pump.

4. In the apparatus as claimed in claim 1, the improvement including means for receiving at least one electrically operable heater in the metal block.

5. In the apparatus as claimed in claim 1, the improvement wherein a gas filter is housed in the metal block.

6. In the apparatus as claimed in claim 1, the improvement wherein the suction pump is a diaphragm pump.

7. In the apparatus as claimed in claim 1, the improvement wherein the metal block is completely surrounded by insulation.

8. In the apparatus as claimed in claim 1, the improvement wherein the metal block is provided with a connection for a hydrocarbon-free gas and a connection for a gas of a defined hydrocarbon concentration apart from the connections for the combustion gas of the hydrocarbon detector.

9. In the apparatus as claimed in claim 1, the improvement wherein means is provided to release a signal if the quantity of the gas sample withdrawn from the process chamber fails to reach a predetermined value.

10. In the apparatus as claimed in claim 1, the improvement wherein means is provided to monitor the output signal of the detector is for a desired value so as to emit an alarm signal upon failure of the detector or the suction pump.

11. In the apparatus as claimed in claim 1, the improvement wherein at the pressure end of the suction pump the supply conduits are divided into two conduits, a first one thereof leading to the detector and a second one to a process chamber.

12. In the apparatus as claimed in claim 11, the improvement wherein a pressure switch is provided at the pressure end of the suction pump to emit a disturbance signal upon dropping of the pump pressure head.

13. In the apparatus as claimed in claim 12, the improvement wherein a pressure reducer is provided to stabilize the pressure at the pressure end of the suction pump and to maintain the gas flow constant in the first conduit.

14. In the apparatus as claimed in claim 11, the improvement wherein means is provided to pass a greater amount of gas through said second conduit than through the first one.

15. In the apparatus as claimed in claim 11, the improvement wherein the first and/or second conduit each include a capillary tube therein.

16. In an apparatus for measuring the hydrocarbon concentration in a hot gas sample withdrawn from a process chamber and for generating an electric monitoring signal in accordance with said concentration, said apparatus having a tempered sampling probe adapted to be introduced into a process chamber, a hydrocarbon detector arranged outside of a process chamber adjacent a wall thereof, a suction pump having a suction end and a pressure end for withdrawing the gas sample from a chamber, a thermally insulating casing enclosing the detector and suction outside a process chamber, the improvement comprising: a solid metal tempered block means enclosed in the casing, said block means being mounted against a wall of a process chamber and containing an opening in direct communication with an opening in a process chamber through which gas is to be withdrawn, said block means further containing therein the detector and suction pump and having bores therein defining supply conduit means leading from said opening therein for directing gas from a process chamber, through said suction pump from the suction end thereof to the pressure end and then to said detector, said supply conduit means further being divided on the pressure end of said suction pump into a first conduit leading to said detector and a second conduit leading back to a process chamber, and means for controlling the rate of flow of gas through said second conduit to maintain a constant flow of gas in said first conduit.

* * * * *